United States Patent [19]

Takita et al.

[11] 4,294,770

[45] Oct. 13, 1981

[54] PROCESS FOR PREPARING A NORMAL LONG CHAIN ALKANOIC ACID

[75] Inventors: Hitoshi Takita; Yutaka Mukaida, both of Tokyo; Satoru Enomoto, Fujisawa, all of Japan

[73] Assignee: Kureha Kagaku Kogyo Kabushiki Kaisha, Tokyo, Japan

[21] Appl. No.: 121,875

[22] Filed: Feb. 15, 1980

[30] Foreign Application Priority Data

Feb. 22, 1979 [JP] Japan .................................. 54-19998

[51] Int. Cl.$^3$ .............................................. C11C 1/00
[52] U.S. Cl. .................................................. 260/413
[58] Field of Search ........ 260/413 R, 413 HC, 413 S; 562/541

[56] References Cited

PUBLICATIONS

Survey of Organic Synthesis, Wiley Inc., N.Y. (1970) pp. 754–755.
Survey of Organic Synthesis (1970) pp. 22–23, 365–366.

*Primary Examiner*—John F. Niebling
*Attorney, Agent, or Firm*—Wegner & Bretschneider

[57] ABSTRACT

Disclosed herein is a process for preparing a normal long chain alkanoic acid having 26 to 36 carbon atoms, in which a trihalogenomethane is added to a normal alpha-olefin having 25 to 35 carbon atoms in the presence of a radical initiator and then the thus formed 1,1,1-trihalogenoalkane is hydrolyzed with an alkali to convert into the normal long chain alkanoic acid.

4 Claims, No Drawings

PROCESS FOR PREPARING A NORMAL LONG CHAIN ALKANOIC ACID

The production of a normal long chain alkanoic acid according to this invention is indicated by the following reaction formulae:

Step 1.

$$CH_3(CH_2)_nCH_2X + CH_2=CH(CH_2)_8CH_2MgX$$

or $$CH_3(CH_2)_nCH_2MgX + CH_2=CH(CH_2)_8CH_2X$$

$$\rightarrow CH_3(CH_2)_{n+10}CH=CH_2 \quad (I)$$

Step 2.

$$CH_3(CH_2)_{n+10}CH=CH_2 + CHX_3 \xrightarrow{\text{radical initiator}} CH_3(CH_2)_{n+12}-CX_3$$
$$\qquad\qquad (I) \qquad\qquad\qquad\qquad\qquad\qquad (II)$$

Step 3.

$$CH_3(CH_2)_{n+12}-CX_3 + H_2O \xrightarrow{\text{hydrolysis}} CH_3(CH)_{n+12}COOH$$
$$\qquad (II) \qquad\qquad\qquad\qquad\qquad (III)$$

Note:
in the formulae, n is an integer from 12 to 22 and X represents Cl, Br or I.

BACKGROUND AND DETAILED DESCRIPTION OF THE INVENTION

The present invention relates to a novel process for preparing a normal long chain alkanoic acid. Particularly, this invention relates to a novel process for preparing a normal long chain alkanoic acid having more than 26 carbon atoms by adding a trihalogenomethane to a normal alpha-olefin (I) having more than 25 carbon atoms in the presence of a radical initiator to form a 1,1,1-trihalogenoalkane (II) having more than 26 carbon atoms, and then hydrolyzing the compound (II) in an alkaline medium into the normal long chain alkanoic acid (III) having more than 26 carbon atoms.

The normal long chain alkanoic acids having more than 26 carbon atoms are useful as intermediate materials for producing agricultural chemicals and pharmaceuticals, and normal long chain alkyl alcohols obtainable by reducing such a normal long chain alkanoic acid, for instance, triacontanol has recently been given attention as a compound having a growth-controlling function to plants and fungi belonging to the class Basidiomycetes.

As a method for synthesizing a normal higher alkanecarboxylic acid, methods have hitherto been known in which at first a ketoacid is synthesized as an intermediate substance and it is reduced to be the normal long chain alkanoic acid, and the methods are reported in literatures, for instance, R. G. Jones, J. Am. Chem. Soc., 69, 2350 (1947); A. Watanabe, Bull. Chem. Soc., Japan, 32, 1295 (1959); A. Watanabe, ibid., 33, 531 (1960).

However, it is hardly said that the above-mentioned methods are idustrially applicable methods because of its use of a specified raw material and of the plurality of steps of the above-mentioned method including complicated reactions.

The inventors, considering the above-mentioned problems, studied the possible methods for producing ther normal long chain alkanoic acid from an easily available raw material in a few number of steps in excellent yield, and then have arrived at this invention.

This is, the present invention offers a novel process for preparing a normal long chain alkanoic acid having 26 to 36 carbon atoms, comprising: bringing a trihalogenomethane into reaction with a normal alpha-olefin having 25 to 35 carbon atoms in the presence of a radical initiator to obtain a 1,1,1-trihalogenoalkane; and hydrolyzing said 1,1,1-trihalogenoalkane with an alkali thereby to obtain said normal long chain alkanoic acid. For instance, a normal alkyl halide is cross-coupled with 1-halogenoundecene-10 in a Grignard's reaction to obtain a normal alpha-olefin (I). The normal alkyl halide is represented by the formula: $CH_3(CH_2)_nCH_2-X$ wherein X is Cl, Br or I; and n is an integer of from 12 to 22. The normal alpha-olefin produced in petrochemistry may be used as the compound (I). The compound (I) is reacted with a trihalogenomethane in the presence of a radical initiator to obtain 1,1,1-trihalogenoalkane (II) having 26 to 36 carbon atoms, and then the compound (II) is hydrolyzed in an alkaline medium to convert into a normal long chain alkanoic acid (III) having 26 to 36 carbon atoms. The followings are the detailed explanation of the present invention.

The normal alpha-olefin having more than 25 carbon atoms (I) for use in this invention is, for instance, obtained by the above-mentioned step (1) or obtained by polymerizing ethylene.

As an example of the step (1), either a normal alkyl halide having more than 14 carbon atoms (represented by the formula: $CH_3(CH_2)_nCH_2-X$), or 1-halogenoundecene-10 may be converted into the corresponding Grignard reagent. The Grignard reagent is made to cross-couple with either 1-halogenoundecene or the normal alkyl halide. As the starting material, normal alkyl halide having 14 to 24 carbon atoms and Cl, Br or Cl as a halogen, preferably Cl or Br.

In addition, the 1-halogenoundecene-10 is 1-chloroundecene-10, 1-bromoundecene-10 or 1-iodoundecene-10. The above-mentioned cross-coupling is carried out in an ether-type solvent, for instance, diethyl ether or tetrahydrofuran at a temperature of $-78°$ to $30°$ C., preferably of $-10°$ to $15°$ C. In order to carry out the cross-coupling smoothly, it is preferable to add a copper compound, for instance, CuBr or $Li_2CuCl_4$ to the reaction system. The amount of the addition is 0.1–1.0 mol of the compound per mol of the Grignard reagent.

The addition of the normal alpha-olefin to the trihalogenomethane of this invention is carried out according to the step (2) above-mentioned. As the trihalogenomethane represented by the formula $CHX_3$, chloroform, bromoform or iodoform is used. The above-mentioned addition reaction may be also carried out at a raised temperature, however, for fear of the frequent side reactions, it is preferably carried out at a relatively low temperature, for instance, 40° to 100° C. for at least longer than 5 hours. The radical initiator is not necessary limited and, for instance, acetyl peroxide, benzoyl peroxide, lauroyl peroxide, azobisisobutyronitrile or ultraviolet rays may be used. The amount of the radical initiator is preferably 0.05 to 0.15 mol per mol of the normal alpha-olefin (I) for use in the reaction.

The intermediate product of Example 1 of this invention, i.e., 1,1,1-trichlorotriacontane, $CH_3(CH_2)_{28}$—$CCl_3$, is a novel compound.

The step (3) is hydrolysis of a 1,1,1-trihalogenoalkane (II) having more than 26 carbon atoms and, via this step, a normal long chain alkanoic acid is produced.

The hydrolysis of this invention does not so easily proceed as in the cases of lower trihalogenoalkanes. Using an aqueous alkali solution at a temperature of 100° C., the reaction did not proceed substantially in the case of compound (II) within 20 hours. On the other hand, the reaction proceeds by the use of an acid catalyst such as sulfuric acid and nitric acid. However, in this case, the yield of the object compound is poor because of the formation of by-products in large amounts. Further, in the case where the reaction is carried out in a uniform solvent mixture such as a system of dimethylsulfoxide and an aqueous alkali solution, although the reaction proceeds, it is also difficult to obtain the object alkanoic acid in high yield due to the accompaniment of de-carboxylation of the carboxylic acid formed.

Meanwhile, the carrying out the hydrolysis of trihalogenoalkane in the interphase between an organic phase and an aqueous phase, the object alkanoic acid is obtained extremely effectively. Actually, in the case where an organic solution containing the dissolved trihalogenoalkane and an aqueous alkali solution are made to react under agitation, the object product is obtained from the reaction mixture in a state of suspension or emulsion.

Although the reaction mechanism has not been elucidated, however, such a phenomenon is presumably attributed to the structure of higher order and the specific properties of the chain compound with a large number of carbon atoms.

In the present invention, the hydrolysis is generally carried out at a temperature of 20° to 120° C., preferably 40° to 100° C. Higher the temperature, the fear of decarboxylation is the larger, and lower the temperature, the longer the time period for completion of the reaction.

As the alkali, a hydroxide of an alkali metal such as sodium hydroxide, potassium hydroxide, etc. may be used.

As the organic solvent for use in the present invention, the solvent which is not completely miscible with water is preferable. For instance, that is an alcohol such as n-butyl alcohol, isobutyl alcohol, 1-pentanol, isoamyl alcohol, sec-amyl alcohol, 3-pentanol and tert-amyl alcohol. Furthermore, that is a saturated hydrocarbon having a relatively low boiling point such as butane, pentane and hexane. In addition, an emulsifier may be added to the reaction system.

As has been described above, the present invention has made it possible to easily obtain a normal long chain alkanoic acid having more than 26 carbon atoms, useful as a raw material for producing the normal long chain alcohols used as an intermediate product for agricultural chemicals and pharmaceuticals or the plant-growth controlling agent, and accordingly the present invention has contributed much in industrial and agricultural fields.

The followings are the more detailed explanation while referring to Examples.

EXAMPLE 1

(1—1) Synthesis of nonacosene-1

In a three-necked round-bottomed flask of 2 liter of capacity with nitrogen-substituted atmosphere, 57.9 g (0.174 mole) of stearyl bromide and 390 ml of tetrahydrofuran purified by distillation after dehydration were introduced, and the flask was immersed into a bath of a controlled temperature of $-2°$ to $0°$ C. Then, a 0.1 molar tetrahydrofuran solution of $Li_2CuCl_4$ was introduced into the flask, and an ethereal solution of undecenylmagnesium bromide of the total amount of 0.193 mole was added to the content of the flask to make a reaction. After a predetermined period of reaction, an aqueous 5 N sulfuric acid solution was added to the reaction mixture, and the reaction product was extracted with ether. After drying the extract solution, the solvent was distilled off to obtain the colourless, transparent oily reaction product as the residue. The rate of conversion and the rate of selectibity of the reaction were determined by the analysis of the reaction product with gas-liquid chromatography (abbreviated as GLC hereinafter) and shown in Table 1.

TABLE 1

| No. of Experiment | Time period of reaction | Rate of conversion* | Rate of selectivity |
|---|---|---|---|
| 1 | 3 hours | 27.07% | 100% |
| 2 | 9 hours | 56.71% | 100% |
| 3 | 20 hours | 74.56% | 100% |

Note:
*Rate of conversion to the coupling reaction product based on stearyl bromide.

The product of the coupling reaction, i.e., nonacosene-1 was isolated by distillation under reduced pressure.

The values of physical properties of nonacosene-1 obtained by the procedure in Example 1—1) of the present invention were as follows:

Elementary analytical values of C: 84.90%, H: 14.10%, (theoretical values of C: 85.62%, H: 14.37;1 %).

Boiling point: 209°–214° C./0.2 mmHg

Melting point: 61°–63° C.

Mass spectrographic data: m/e 406

From the above-mentioned values, the product was identified with nonacosene-1.

(1-2) Synthesis of 1,1,1-trichlorotriacontane

In a 300-ml three-necked round-bottomed flask, 10 g (24.6 m mole) of nonacosene-1 and 170 ml of chloroform were placed, and after the atmosphere of the flask was substituted with nitrogen, 5 ml of chloroform containing 0.58 g (2.4 m mole) of dissolved benzoyl peroxide therein was dissolved into the content of the flask. After heating the solution by a bath of a temperature of 60° to 65° C. for 38 hours under reflux, the solution was cooled to room temperature and was washed with an aqueous saturated sodium hydrogen carbonate solution. Then, after drying the washed solution with anhydrous magnesium sulfate, solvent was distilled off from the dried solution to obtain the reaction product weighing 12.95 g. The rate of conversion and the rate of selectivity of the reaction determined by GLC of the reaction product were respectively, 98.35% and 100%. The purified product obtained by recrystallization of the reaction product from acetone showed the following values of physical properties:

Elementary analytical values of C: 68.50%, H: 11.10%, Cl: 20.35% (theoretical values of C: 68.48%, H: 11.30%, Cl: 20.22%).

Melting point: 53.5°–54.0° C.

Molecular weight: 530.2, (theoretical value: 525.5 calculated as the atomic weigh of Cl being 35.5)

From the above-mentioned results, the reaction product was identified with 1,1,1-trichlorotriacontane.

EXAMPLE 2

In accordance with (1—1) and (1-2) of Example 1, using eicosanyl bromide and undecenylmagnesium bromide as the raw material, a similar reaction was carried out to obtain hentriacontane as the intermediate product and then by another reaction 1,1,1-trichlorodotriacontane was obtained. One gram of the thus obtained, 1,1,1-trichlorodotriacontane dissolved in 6 ml of n-butyl alcohol was placed in a 50-ml conical flask and 1.4 ml of distilled water and 2.5 g of potassium hydroxide were added to the solution in the flask. The mixture was heated to a temperature of 60° C. to make reaction for 30 hours under agitation. Then, iced water was added to the reaction mixture to cool the mixture, and after neutralizing with an aqueous dilute hydrochloric acid, the separated precipitate was collected by filtration and dried to obtain 0.82 g of the product. After recrystallizing from benzene, 0.52 g of dotriacontanoic acid melt-

TABLE 2

| The series of reaction | No. of experiment | Kind of basic solution | Solvent | Reaction temperature | Reaction period | Rate of conversion | Rate of selectivity of the acid* |
|---|---|---|---|---|---|---|---|
| The present invention | 3 | KOH:H$_2$O = 25:41* | n-butyl** alcohol | 80–85° C. | 6 (hours) | 100% | 31.1% |
| | 4 | " | n-butyl** alcohol | 60–65° C. | 37 | 100 | 72.2 |
| | 5 | " | n-butyl** alcohol | 50° C. | 40 | 100 | 80.2 |
| | 6 | " | n-butyl** alcohol | 40° C. | 50 | 70 | 90.3 |
| Comparative examples | 1 | " | not used | 100° C. | 22 | 0 | 0 |
| | 2 | " | " | 100° C. | 62 | 0 | 0 |
| | 3 | " | dimethyl-sulfoxide*** | 55–60° C. | 1 | 0 | 0 |
| | 4 | " | dimethyl-sulfoxide*** | 55–60° C. | 19 | 100 | 0 |
| | 5 | CaCO$_3$:H$_2$O = 25:88* | not used | 100° C. | 16 | 0 | 0 |
| | 6 | KOH:H$_2$0 = 25:41 | n-butyl** alcohol | 120° C. | 4.5 | 100 | 0 |

Notes:
*mole equivalent to trichlorotriacontane;
**amount was 6 ml;
***amount was 5 ml.

(1-3) Production of triacontanoic acid

In a 50-ml egg-plant type flask, each one of the aqueous solutions shown in Table 2 was charged, and then 1.0 g of 1,1,1-trichlorotriacontane and one of the organic solvents shown also in Table 2 were added to the solution in the flask, and hydrolysis of 1,1,1-trichlorotriacontane was carried out under agitation under the conditions shown also in Table 2. The results are also shown in Table 2. The products obtained under the conditions shown in Table 2 with the products of the comparative examples 4 and 6 consisted almost solely of nonacosane formed by decarboxylation.

The reaction mixtures obtained according to the process of the present invention were treated by separation to give raw products. The purified products obtained by recrystallization from benzene gave the following values of elementary analytical data and the melting point:

Elementary analytical values of C: 80.75% and H: 13.30% (theoretical values of C: 79.58% and H: 13.36%)

Melting point: 93.5° C.

According to the above-mentioned results, the reaction product was identified with triacontanoic acid.

ing at 95.5° C. was obtained with a yield of 60%.

EXAMPLE 3

In a 100-ml conical flask, a solution of 13.5 g of potassium hydroxide in 7 ml of distilled water was prepared while heating, and 30 ml of n-butyl alcohol and 49.67 g (0.0095 mole) of 1,1,1-trichlorotriacontane were added to the solution in the flask, and the mixture was heated to 60°–65° C. while agitating to make reaction. The reaction system showed a dispersed state of oil in water due to the agitation and after 10 minutes of the commencement of the reaction, the solution became orange-red in colour. In a moment of stopping the agitation, an oily layer separated from the dispersion. The reaction mixture obtained by agitating for 16 hours under the above-mentioned temperature condition, after cooling, was added to about 250 ml of iced water to obtain a separated precipitate. After dispersing the precipitate well in the aqueous medium, the medium was acidified by adding a dilute hydrochloric acid and the precipitate was collected by filtration and repeatedly washed with methanol. The washed precipitate was dried to be a raw product weighing 4.30 g. After dissolving the raw product into about 20 ml of benzene and removing an extremely small amount of insoluble matters by filtration, it was recrystallized to be 2.586 g of triacontanoic acid at a yield of 61%. The by-products contained in the filtrate of the recrystallization were mainly nonacosane followed by others, all of them accompanying with the de-carboxylation. The reaction conditions and the results of the above-mentioned reaction are shown in Table 3.

TABLE 3

| Examples | Example 3 | Example 4 | Example 5 |
|---|---|---|---|
| 1,1,1-trichloro-triacontane | 4.967 g (0.0095 mole) | 12.6 g (0.024 mole) | 10.0 g (0.019 mole) |
| n-butyl alcohol | 30 ml | 76 ml | 60 ml |
| Alkali | 13.5 g of KOH | 12.6 g of NaOH | 20.0 g of NaOH |
| Distilled water | 7.0 ml | 17.6 ml | 14.0 ml |
| Reaction temperature | 60–65° C. | 60–62° C. | 60–62° C. |
| Reaction period | 16 hours | 24 hours | 30 hours |
| Product   crude product | 4.3 g | 10.8 g | 8.6 g |
| Triacontanoic acid(purified) | 2.586 g yield of 61% | 8.8 g of 81% | 6.44 g of 75% |

EXAMPLES 4 and 5

As in Example 3, 1,1,1-trichlorotriacontane dissolved in n-butyl alcohol was hydrolyzed with an aqueous sodium hydroxide solution of the concentration shown in Table 3, and after obtaining the crude product, triacontanoic acid was obtained by recrystallizing the crude product from benzene, the reaction conditions and the product being shown also in Table 3.

What is claimed is:

1. A process for preparing a normal alkanoic acid of 26 to 36 carbon atoms comprising the steps of heating a mixture of 1,1,1-trihalogeno-normalalkane of 26 to 36 carbon atoms dissolved in an organic solvent which is not completely miscible with water and an aqueous alkali solution to a temperature of 40° to 100° C. while stirring said mixture, thereby hydrolyzing said 1,1,1-trihalogeno-normalalkane into an alkali normalalkanoate, and neutralizing said alkali normalalkanoate, thereby obtaining said normal alkanoic acid of 26 to 36 carbon atoms.

2. A process according to claim 1, wherein said organic solvent is selected from the group consisting of butanes, pentanes, hexanes, n-butyl alcohol, isobutyl alcohol, 1-pentanol, isoamyl alcohol, sec-amyl alcohol, tert-amyl alcohol and 3-pentanol.

3. A process according to claim 1, wherein said alkali is selected from the group consisting of lithium hydroxide, sodium hydroxide and potassium hydroxide.

4. A method according to claim 1, wherein said normal alkanoic acid is triacontanic acid.

* * * * *